United States Patent [19]
Sims et al.

[11] Patent Number: 5,954,695
[45] Date of Patent: Sep. 21, 1999

[54] MULTI-DOSE SYRINGE DRIVER

[75] Inventors: Nathaniel M. Sims, Wellesley Hills; Michael H. Wollowitz, Somerville; David M. Wrightson, Andover, all of Mass.

[73] Assignee: The General Hospital Corporation, Boston, Mass.

[21] Appl. No.: 09/030,093

[22] Filed: Feb. 25, 1998

Related U.S. Application Data

[63] Continuation of application No. 08/696,479, Aug. 14, 1996, Pat. No. 5,722,956
[60] Provisional application No. 60/002,771, Aug. 24, 1995.

[51] Int. Cl.[6] ................................................. A61M 37/00
[52] U.S. Cl. ................................ 604/131; 128/DIG. 12
[58] Field of Search .................................. 604/131, 134, 604/135, 154, 155, 151, 207, 224, 208; 128/DIG. 12

[56] References Cited

U.S. PATENT DOCUMENTS

| | | | |
|---|---|---|---|
| 2,632,445 | 3/1953 | Kas, Sr. ................................. | 128/218 |
| 4,059,110 | 11/1977 | Wuthrich et al. ...................... | 128/218 |
| 4,132,231 | 1/1979 | Puccio ................................... | 128/218 |
| 4,202,333 | 5/1980 | Thill et al. ............................. | 128/218 |
| 4,298,000 | 11/1981 | Thill et al. ............................. | 128/218 |
| 4,430,079 | 2/1984 | Thill et al. ............................. | 604/154 |
| 4,465,478 | 8/1984 | Sabelman et al. ..................... | 604/224 |
| 4,498,904 | 2/1985 | Turner et al. ......................... | 604/211 |
| 4,544,369 | 10/1985 | Skakoon et al. ...................... | 604/155 |
| 4,547,189 | 10/1985 | Moore et al. .......................... | 604/136 |
| 4,597,754 | 7/1986 | Thill et al. ............................. | 604/154 |
| 4,608,042 | 8/1986 | Vanderveen et al. .................. | 604/81 |
| 4,636,197 | 1/1987 | Chu ...................................... | 604/131 |
| 4,652,260 | 3/1987 | Fenton ................................... | 604/67 |
| 4,676,122 | 6/1987 | Szabo et al. ........................... | 74/625 |
| 4,804,368 | 2/1989 | Skakoon et al. ...................... | 604/155 |
| 4,943,279 | 7/1990 | Samiotes et al. ...................... | 604/151 |
| 5,004,124 | 4/1991 | Stefaniak et al. ...................... | 222/136 |
| 5,092,842 | 3/1992 | Bechtold et al. ....................... | 604/135 |
| 5,140,862 | 8/1992 | Pappalardo ............................ | 73/866 |
| 5,176,646 | 1/1993 | Kuroda .................................. | 604/154 |
| 5,232,459 | 8/1993 | Hjertman ............................... | 604/208 |
| 5,300,041 | 4/1994 | Haber et al. ........................... | 604/207 |
| 5,318,539 | 6/1994 | O'Neil ................................... | 604/118 |
| 5,328,486 | 7/1994 | Woodruff ............................... | 604/208 |
| 5,429,607 | 7/1995 | McPhee ................................. | 604/131 |
| 5,599,315 | 2/1997 | McPhee ................................. | 604/218 |
| 5,722,956 | 3/1998 | Sims et al. ............................. | 604/131 |

*Primary Examiner*—John D. Yasko
*Attorney, Agent, or Firm*—Nutter, McClennen & Fish, LLP

[57] ABSTRACT

A syringe driver device is able to effect the controlled, parenteral infusion of a medical fluid using an available disposable syringe. The driver device includes a frame heaving a movable carriage, which houses a force applying element, mounted thereto. A disposable syringe mounts upon the frame and a lengthy microbore tubing attaches to the outlet tip of the syringe. As a force is applied to the syringe plunger, fluid is expelled from the syringe, but its flow rate is dependent upon the diameter of the microbore tubing. The driver device enables the delivery of multiple, sequential doses of fluid.

17 Claims, 10 Drawing Sheets

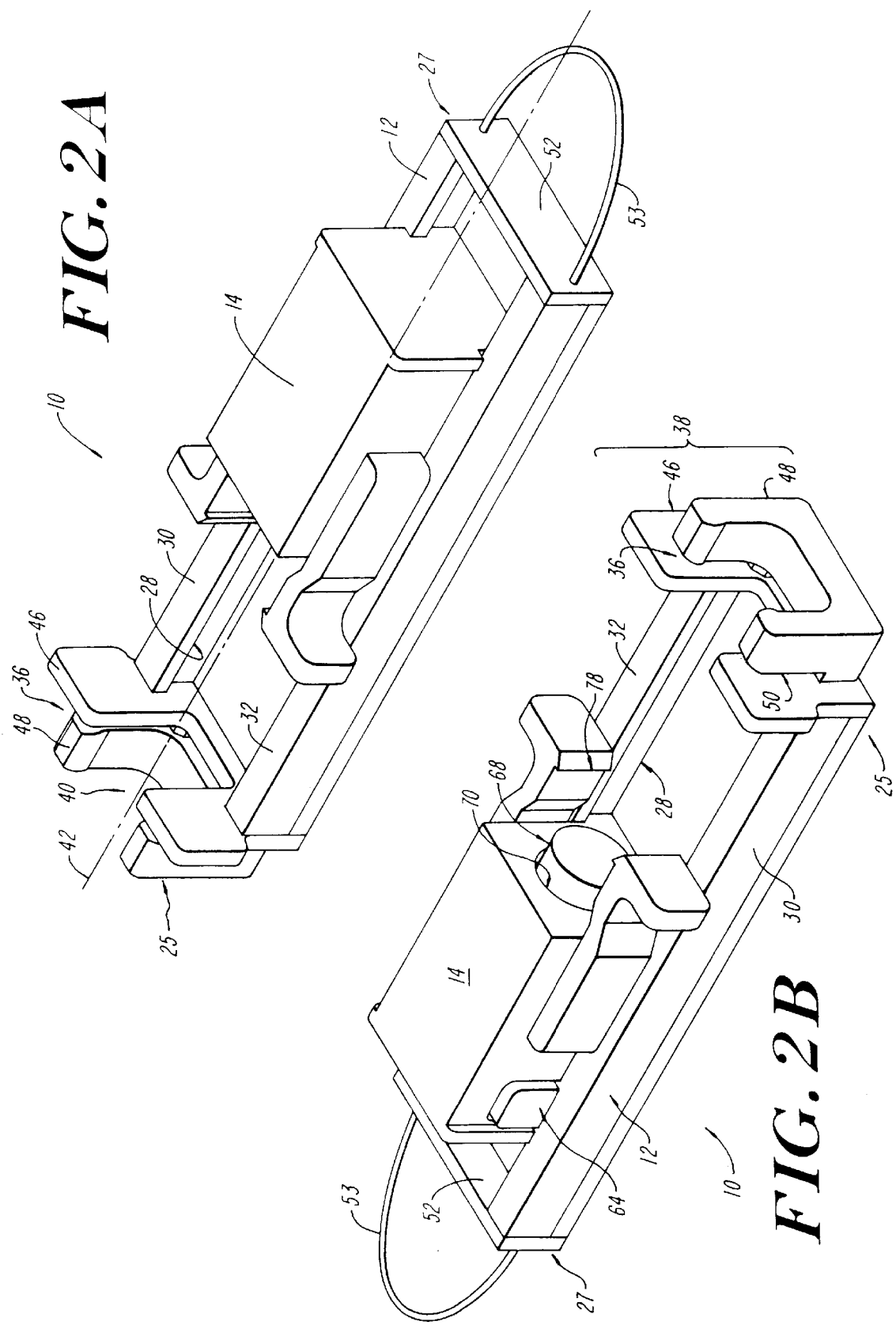

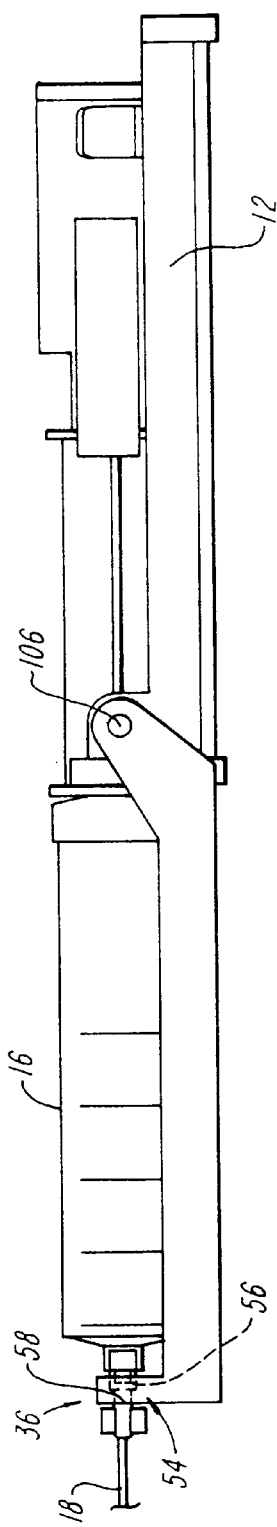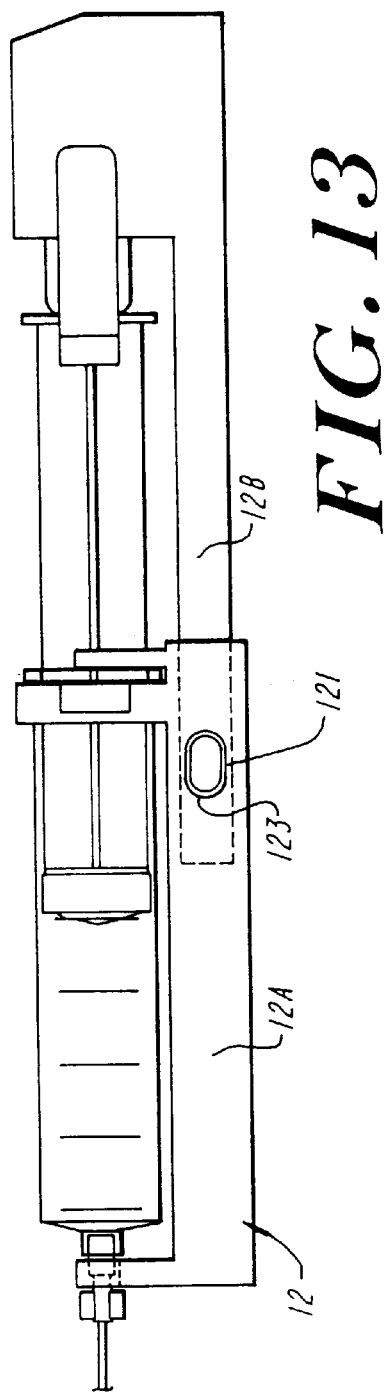
FIG. 12
FIG. 13

MULTI-DOSE SYRINGE DRIVER

CROSS-REFERENCE TO RELATED APPLICATIONS

This application is a continuation of application Ser. No. 08/696,479, filed Aug. 14, 1996, issue as U.S. Pat. No. 5,722,956, now which is based upon U.S. Provisional Patent Application Ser. No. 60/002771 filed Aug. 24, 1995.

BACKGROUND OF THE INVENTION

The invention relates to syringe drivers and systems for effecting a controlled infusion of a medical fluid from a syringe.

Certain medical fluids are administered by controlled parenteral infusion and require a slow but non-rate critical flow. Infusion of a medical fluid in this manner has been generally accomplished by use of a drip bag gravity-feed system or an electronic infusion pump. The drip bag provides non-rate critical flow with a simple and relatively inexpensive apparatus.

In certain applications, particularly those involving small fluid volumes, the use of disposable syringes is preferred to drip bags. The disposable syringe is a commodity item. Syringes may be prepared in large quantities and stored for later use, thereby reducing costs and providing greater reliability and repeatability of preparation. Also, a single syringe may be used to provide multiple doses, simply by advancing the syringe plunger in fixed increments. For example, it may be desired to fill a 60 cc syringe with 40 cc of fluid and to then administer the fluid in 10 cc doses, with a flow rate such that a single dose is delivered in twenty to forty minutes. Doses may then be repeated at fixed intervals, with four doses being delivered from a single disposable syringe.

There exist several advantages to delivering multiple doses from a single dose delivery system. A single large syringe is less expensive than several small syringes or other single dose devices. Significant time savings can be realized in filling, handling, and administering the syringes since the overall number of operations is greatly reduced. There may also be a decrease in patient risk due to the fact that the intravenous delivery system must be opened fewer times for component changes, and so there are fewer opportunities for contamination or handling errors.

Administration of medical fluids at a low flow rate using a syringe is generally accomplished by the use of a syringe pump. A typical syringe pump is a motorized, programmable device on which a syringe is mounted, and which expels fluid from the syringe by advancing the syringe plunger at a controlled rate. The motorized pump advances the syringe plunger at a predetermined velocity, applying force as required to maintain this velocity. The flow rate is therefore independent of fluid resistance unless the resistance becomes so high that the pump cannot safely provide the corresponding force required. The advantages of using disposable syringes for non-rate critical applications are diminished by the cost and complexity of existing syringe pumps. Typical pumps are battery powered, microprocessor controlled, provide numerous programming options and annunciators, and require detailed operator training and ongoing maintenance and inspection. Much of the cost and complexity of the syringe pump is directed to the requirements of rate critical applications and is not required for non-rate critical applications. See, U.S. Pat. Nos. 4,804,368 (Skakoon); 4,544,369 (Skakoon); and 4,943,279 (Samiotes).

Several devices have been developed that are intended to provide less complex and expensive means of providing non-rate critical infusion with a disposable syringe. One option is to replace the electronic components of a typical infusion pump with a spring driven clockwork mechanism. While this type of device has been described, no actual devices are known to have been commercialized. See, U.S. Pat. Nos. 4,059,110 (Wuthrich) and 4,676,122 (Szabo).

A second option is based the use of a predetermined force, rather than a predetermined velocity, that is applied to the syringe plunger so that fluid resistance acts to control the flow rate. This force may be applied by a simple mechanism, such as a weight, or compressed or extended spring of appropriate stiffness. See, U.S. Pat. No. 4,132,231 (Puccio). By appropriate selection of applied force and fluid resistance, the resulting flow rate can be engineered to a desired level. Fluid resistance may be controlled by varying the length and internal diameter of the tubing that connects the syringe to the patient. Appropriate tubing for this application is known as precision microbore tubing because it has a significantly smaller bore diameter than standard tubing used with drip bags or motorized pumps, and because it is manufactured to defined tolerances and specific end points having to do with resistance to fluid flow.

A commercial device based on this alternative is the "Medifuse" device available from 3M Healthcare. In this device, a "Neg'ator" rolled spring is used to apply an approximately constant force to a syringe plunger. This is combined with a selection of microbore tubing sizes, each with a different internal diameter to provide control of flow rate. A somewhat complicated roller and track mechanism is required to counteract the applied torque that is a consequence of the use of the "Neg'ator" spring. The "Medifuse" device functions as intended but its applicability is limited because it does not provide control of multiple doses from a single syringe. The "Neg'ator" spring, because of its rolled design, is susceptible to changes in spring force due to contamination by sticky, abrasive, or particulate material. Moreover, a spring of this type may be easily damaged by improper handling during cleaning. An additional limitation is that the activating mechanism for initiating a dose on the "Medifuse" device involves pivoting a large cover component, which can be clumsy and which requires additional clearance. Also, a syringe cannot be mounted within a "Medifuse" device without initiating fluid delivery from the syringe. U.S. Pat. Nos. 4,202,333 (Thill); 4,298,000 (Thill); 4,430,079 (Thill); and 4,597,754 (Thill).

Another commercial device, the "Band-It" from I-Flow, Inc., described in U.S. Pat. No. 5,429,607 (McPhee), employs microbore tubing but applies force to the syringe plunger using an elastomeric element, such as a stretched band of latex rubber. This device is extremely simple but, again, does not enable delivery of multiple doses. Also, it does not provide a constant or nearly constant flow rate because the force applied by the elastomeric element varies significantly over the range of plunger travel. This device further requires manual stretching of the elastomeric element and provides no mechanism to assist in this action. Like the "Medifuse" device, a syringe cannot be mounted in a "Band-It" unit without causing fluid to be delivered from the syringe.

Other syringe driver systems and described in U.S. Pat. Nos. 4,636,197 (Chu); 4,608,042 (Vanderveen); and 5,318,539 (O'Neil).

Known mechanical, predetermined force-applying devices are not well suited to the delivery of multiple doses from a single syringe. Conversion of these devices to achieve multiple dose control might be accomplished using removable stops to limit the range of plunger travel. By sequentially removing the stops, the plunger could move in a series of fixed increments. Such stops, however, are not intrinsically safe. It is possible to remove several stops at the same time, or to remove the stops in the wrong order. The result can be an overinfusion condition involving the delivery of two or more doses in a continuous manner.

Another drawback of such devices is that the force applied to the plunger can decrease over the range of travel of the plunger. The result is that successive doses will be delivered from the same syringe at increasingly lower flow rates. Various additional references that describe dose setting include U.S. Pat. Nos. 2,632,445 (Kas); 4,498,904 (Turner); 5,232,459 (Hjertman); 5,300,041 (Haber); 5,328,486 (Woodruff); and 5,092,842 (Bechtold).

SUMMARY OF THE INVENTION

The present invention overcomes the disadvantages of the prior art by providing a driver device for effecting a controlled, parenteral infusion of a medical fluid using an available disposable syringe. The driver device is intended for non-rate critical applications, and provides ease of use, intrinsic safety, robustness, and low cost.

The invention consists of two main components: (i) a syringe driver device within which a syringe is removably mountable and which employs a compressed spring element to apply a driving force to the syringe plunger, and (ii) a length of microbore tubing having a small inner diameter through which fluid flows after exiting the syringe, and which provides resistance to limit the rate of flow. Specific features of the invention facilitate delivery of multiple doses, control of dose volume, easy two-handed operation, and protection against unintentional syringe plunger travel.

In particular, the syringe driver device of the invention includes a frame and a selectively positionable carriage that is slidably mounted on the frame, preferably adjacent to the proximal end of the frame. A force applying element that is preferably disposed in or on the carriage is biased to extend from the distal end of the carriage. Preferably, a spring element, disposed within the carriage, applies a biasing force to the force applying element. Cooperating locking elements are disposed on the frame and carriage to secure the carriage to the frame in a desired position. One or more elements for securing and maintaining a syringe within the frame are associated with the frame.

Desired carriage positions include (i) an unlocked, slidable position; (ii) at least one locked, force applying position in which the force applying element is at least partially retracted within the carriage; and (iii) a locked, non-force applying position in which the force applying element is fully extended from the carriage.

In its operative condition, the syringe driver system constructed according to the present invention includes a syringe, which is secured within the frame, and a microbore tubing assembly secured to the distal end of the syringe. The microbore tubing assembly has proximal and distal ends with a fluid passageway extending there between. The proximal end typically includes a mechanism, such as a "Luer Lock," to facilitate detachable coupling to an outlet end of the syringe. Optionally, a family of microbore tubing assemblies is provided. Additionally, each type of microbore tubing has an internal passageway with a different inner diameter and other characteristics necessary to achieve a specified resistance to fluid flow. Each type of microbore tubing assembly may have an adapter mechanism with a different external geometry and/or dimensions corresponding to a given resistance to fluid flow. The various adapter mechanisms may cooperate selectively with a socket or other engagement means associated with an appropriate driver device having mechanical characteristics suitable to the intended fluid delivery application.

The present invention provides a novel driver device that overcomes problems that are presented by the prior art. An ordinary, compression type coil spring, or a similar means, is employed to provide the driving force to the syringe. However, the spring must be moved and recompressed for the delivery of each dose. This mechanism thus enables the magnitude of the spring force to be maintained for sequential doses. The structure of the device that recompresses the spring for each dose is such that it is not possible to set the device to deliver more than one dose continuously. At the end of the delivery of a dose, any further extension of the spring, and resulting delivery of fluid, is prevented by a non-removable stop so that continuous, "run away" delivery of fluid is not possible. Additionally, at the end of a dose delivery, siphoning or drainage of fluid from the syringe or tubing assembly is prevented by non-removable stops which engage the plunger and the syringe barrel, respectively, to counteract any hydrostatic force which may tend to bias the plunger towards full insertion when the carriage is in the locked, non-force applying position.

Accordingly, the invention provides a driver device for slowly ejecting one or more fluid volumes from a specified medical container (e.g., a syringe) having a rigid barrel, graduated markings, an outlet port, a gripping flange, and a plunger with tip and disk mechanism.

BRIEF DESCRIPTION OF THE DRAWINGS

FIG. 2A is a perspective view from the rear (proximal) end of the syringe driver shown in FIG. 1, without the syringe.

FIG. 2B is a perspective view from the front (distal) end of the syringe driver shown in FIG. 1, without the syringe.

FIG. 12 is a side view of the syringe driver of FIG. 10, in the fully opened position and housing a syringe.

FIG. 13 is a side view of another embodiment of the syringe driver device according to the present invention, having a telescoping frame assembly.

DETAILED DESCRIPTION OF THE INVENTION

Figure 1:
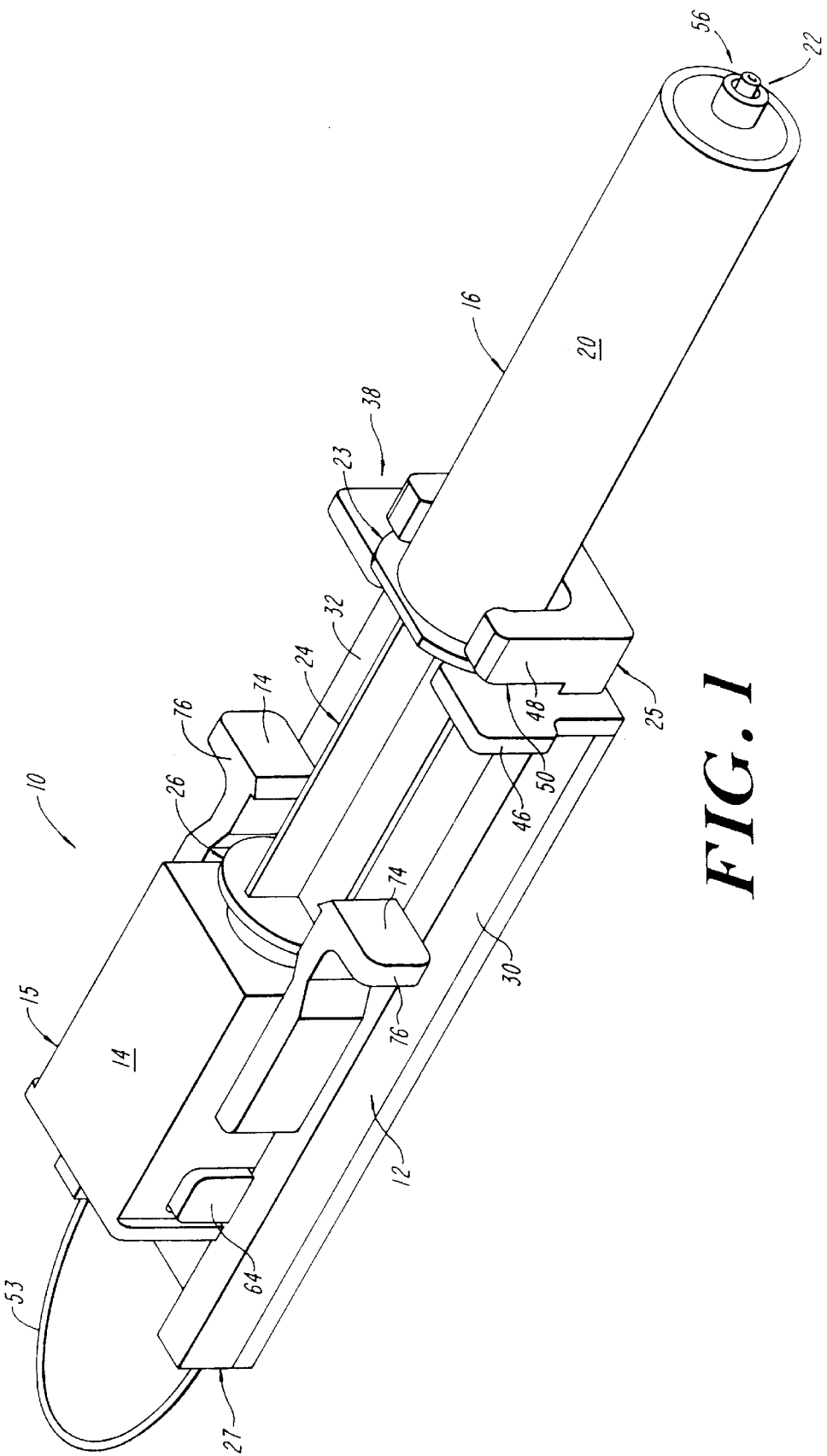
FIG. 1 is a perspective view of a syringe driver assembly constructed according to the present invention.

The syringe driver of the invention is useful to facilitate multiple sequential doses of a fluid, such as a medicament, from a syringe at a controlled, predetermined flow rate. The driver device 10, as illustrated in FIGS. 1–9, comprises a frame 12, a carriage 14, a syringe 16, mounted within the frame, and an outflow tubing assembly 18.

The syringe 16 used with the driver device can be any type of syringe used to dispense medical fluids such as medicaments and the like. The syringe can be of any one of a variety of sizes, ranging, for example, from 5 cc to 60 cc volume capacity. The syringe includes a barrel (with graduated markings) 20, an outlet tip 22 at the distal end of the syringe, which connects to outflow tubing assembly 18, a syringe plunger 24, a syringe flange 23, and a plunger disk 26 at a proximal end of the plunger. The plunger is slidable between withdrawn and inserted positions to expel fluid from within the syringe barrel.

As illustrated, the frame 12 has distal 25, and proximal 27 ends, and comprises a track 28, formed of adjacent, parallel rails 30, 32. A carriage 14 is mounted upon the rails 30, 32 of track 28 at the proximal end 27 of the frame, and is able to slide along the track proximally and distally. The distal end 25 of the frame 12 includes a syringe mounting element 36 which secures the syringe within the frame 12.

FIGS. 1–5 illustrate an embodiment in which the syringe mounting element 36 is a yoke element 38 that mates with the syringe flange 23 to help secure the syringe 20 within the frame 12. The yoke element 38 also acts as an end stop for the carriage motion. The yoke element 38 comprises a longitudinal groove structure 40 for receiving the syringe barrel 24 and plunger assembly. The space separating the adjacent gripping flange 46 and the distal flange 48 forms a transverse slot 50 which is able to engage securely the syringe flange 23, such as through a mechanical fit. The yoke element 38 also serves to prevent movement of the syringe barrel 20, in the proximal or distal directions, relative to the syringe plunger 24.

As illustrated in FIGS. 12 and 13 the syringe mounting element 36 can also be in the form of a socket element 54 which cooperatively engages and supports the distal end 56 of syringe 16 and/or the proximal portion of outflow tubing assembly 18. The socket element 54 is shaped and dimensioned to cooperatively engage the distal end 56 of the syringe. Socket 54 preferably, includes an aperture 58 through which the outlet tip 22 of the syringe, the male luer 67, and the outflow tubing 18 may extend. Alternatively, as shown in FIGS. 14A, 14B, 16, and 17, the socket element 54 may be dimensioned selectively to engage and support an adapter element 34 of the microbore tubing assembly 18 shown in FIGS. 15B and 15C.

The proximal end 27 of the frame 12 includes a stop element 52 for preventing further proximal movement of the carriage 14. Optionally, a hanger device 53 is associated with the stop 52 to enable the apparatus to be suspended.

Figure 4:
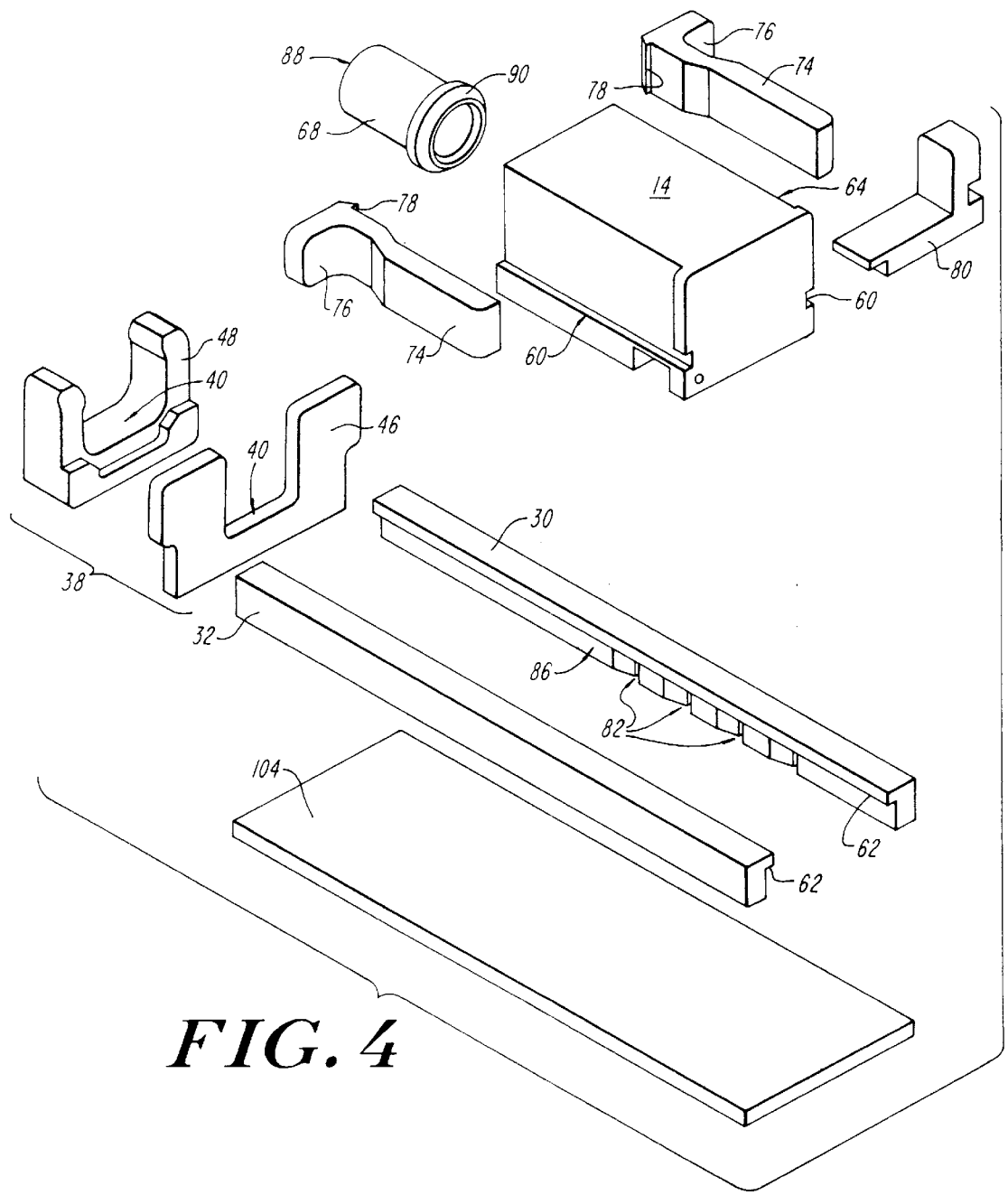
FIG. 4 is an exploded view of the syringe driver device shown in FIG. 2A.
Figures 5, 6:
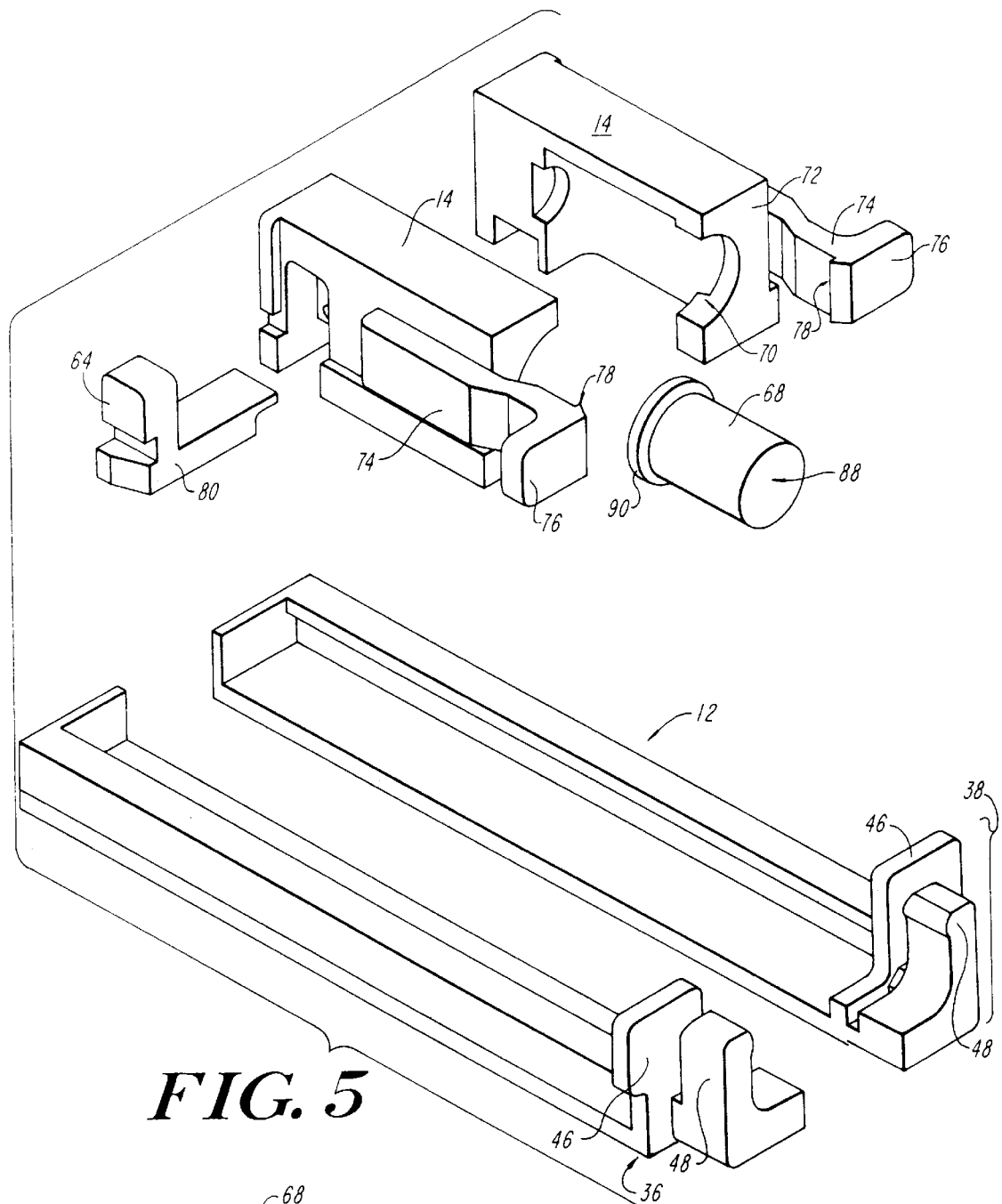
FIG. 5 is an exploded view of the syringe driver device shown in FIG. 2B.
FIG. 6 is a side, sectional view of a force-applying element used with the syringe driver assembly shown in FIG. 1.

As illustrated in FIGS. 2A and 4, the carriage 14 includes a structure that enables the carriage to mount and slide upon rails 30, 32 of frame track 28. In one example the carriage may include a longitudinally oriented slot 60 on each side of the carriage. The slot 60 mates with a horizontal lip 62 formed on each rail 30, 32. This engagement allows the carriage to slide freely on the track 28, while at the same time preventing any vertical, dislodging movement of the carriage.

The carriage 14 comprises a housing 15 which contains a spring element 66. A piston device 68 is displaceably positioned within and is biased to project from an aperture 70 formed in a distal end 72 of the housing. Dual finger grip flanges 74 also extend from the distal end of the housing. Each finger grip flange comprises an outwardly flared finger grip element 76. Further, the interior surface of each finger grip flange includes an anti-siphon latch or stop element 78 that prevents further distal movement of the syringe plunger (relative to the syringe barrel) independent of movement of the carriage or piston 68.

Cooperating locking elements are associated with the carriage 14 and the frame 12 to secure the carriage to the frame. The cooperating locking elements enable the carriage to be secured in the following positions: (i) an unlocked position; (ii) at least one locked, force applying position in which the piston 68 is at least partially retracted within the carriage; and (iii) a locked, non-force applying position in which the piston 68 is fully extended from the carriage.

Figure 8:
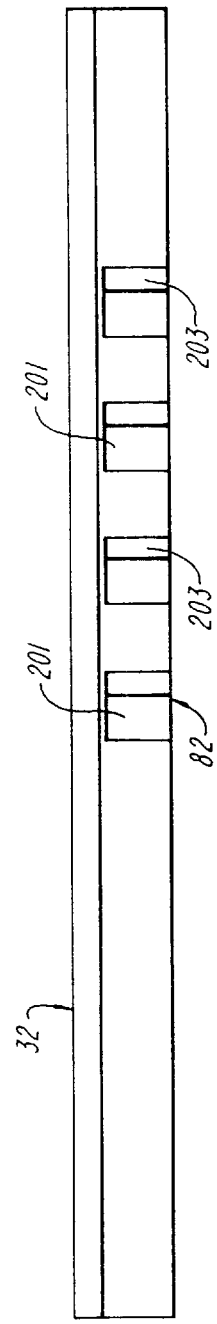
FIG. 8 is a side view of one rail of the track forming the syringe driver assembly of FIG. 1.
Figure 9:
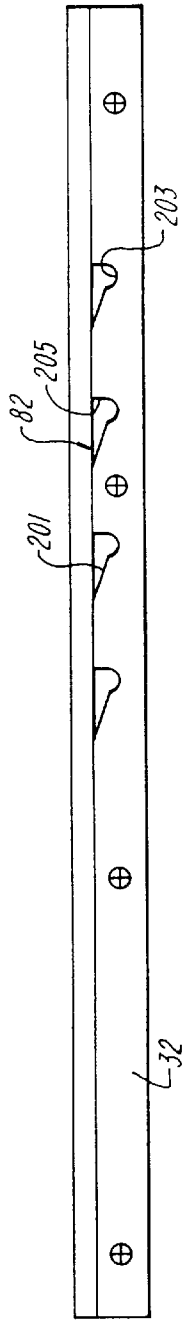
FIG. 9 is a side view of the track shown in FIG. 8, rotated 90 in the clockwise direction about the longitudinal axis of the rail.

In one embodiment, illustrated in FIGS. 1–5, the cooperating locking elements can comprise the combination of a pawl mechanism 80 formed on the carriage and a plurality of detents 82 formed on at least one of rails 30, 32. Detents 82 can be of virtually any useful shape and dimension. FIGS. 8 and 9 illustrate an exemplary detent shape in which a distal part of detents 82 has a wall 201 which angles outwardly at a gradual rate before reaching a rounded out detent area 203 that it bordered, at its proximal end, by wall 205. By way of example, each detent 82 can span a distance, from proximal to distal ends, of about 0.2 to 0.4 inch, and have a depth, at its detent area 203, of about 0.1 to 0.2 inch.

FIGS. 1 through 5 illustrate that the proximal end of the housing contains a release button 64. The release button, which can be mounted on a side of the housing, is a spring loaded pawl mechanism that engages detents or grooves 82 formed in an interior surface of one of rails 30, 32 of the track 28. Compression of the release button 64 retracts the pawl 80 and allows the carriage to move forward (distally) or rearward (proximally) within the track 28. Once the pawl 80 is released it is forced (e.g., by spring biasing) against the interior wall 86 of the rail 30. Linear movement of the carriage is possible until the pawl 80 encounters a detent 82.

As illustrated in FIGS. 4 through 7, the carriage piston 68 can be in the form of a hollow cylinder that is closed at the distal end 88 thereof that projects from the aperture 70 of housing 15. The proximal end of the piston comprises a collar 90 having an increased diameter. The abutment of shoulder 89 of collar 90 with the interior of the wall of the housing, adjacent aperture 70, maintains the piston 68 within the housing in a displaceable condition.

Figure 7:
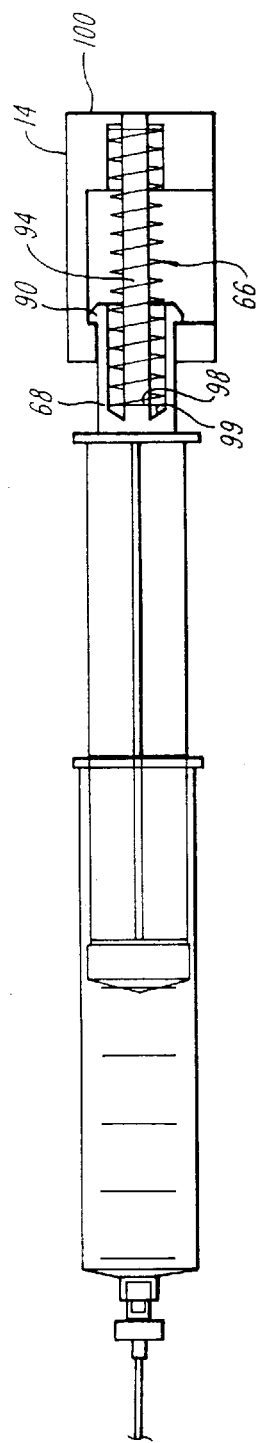
FIG. 7 is a side view, partially cut away, illustrating the internal mechanism of the carriage element of the driver device.

As illustrated in FIG. 7, the interior of the housing 15 optionally includes a dowel 94 which may extend the length of the housing and into the hollow, internal portion of the piston 68. Although not illustrated, the dowel preferably is able to extend through an opening (not shown) in the proximal wall of the housing. FIG. 7 illustrates that a compression spring 66 may be mounted around the dowel 94, which extends from a distal end 98 abutting the interior distal end wall 99 of the piston 68 to the interior proximal wall 100 of the housing. As so configured, the piston is biased by the spring element 96 to the extended position.

As previously described, the driver device is intended to be fitted with a specific syringe and to deliver a single, specific dose of a medical fluid following spring actuation. Such limitations are mainly enforced by (i) the shape and size of the syringe mounting yoke, (ii) the number and locations of ratcheting detents on the track, (iii) the limit of travel of the carriage piston, and (iv) the shape and location of antisiphon stop elements 78.

The syringe mounting element 36 preferably is sized such that a syringe smaller than the correct size for a given driver device will immediately fall out of the driver device, and one of too large a diameter cannot be snapped into place within the driver device. Similarly, a differently proportioned syringe, such as one from a different manufacturer, cannot properly be fitted within the yoke. The syringe mounting element 36 also serves to contact and restrain a portion of the syringe, such as the syringe flange or the distal end of the syringe, to maintain the position of the syringe body longitudinally when force is applied to the syringe plunger, or hydrostatic forces (negative pressure) are applied to the outlet tip 22 by the action of gravity on the column of fluid in the tubing assembly 18.

One of ordinary skill in the art will readily appreciate that by appropriate design of the device, it is possible to provide adaptations to syringes having specific shapes and dimensions, and to adapt the device to deliver different dosages of fluids at various fluid flow rates. The syringe mounting element and the portion of the frame or track containing the detents may be fabricated as separate components that are joined to the remainder of the device during assembly. In addition, a spacer, collar, or other retaining element may be added to the carriage piston to further limit its travel within the housing. In this way, variations of the device may be created with a minimum of additional expense.

An example of one modification is to provide 5 cc, rather than 10 cc, doses for use in pediatric drug delivery. This modification can be accomplished by doubling the number of detents and by adding a collar or other device to limit the travel of the carriage piston to approximately half of its original range.

FIGS. 1–5 illustrate an embodiment of the invention in which the syringe mounting element 36 comprises yoke 38 which engages syringe flange 23. In another embodiment, illustrated in FIGS. 12 and 13, the syringe mounting element 36 comprises a socket element 54 formed at a distal end of the frame 12. Socket element 54 preferably engages a distal end 56 of the syringe 20 while an aperture 58 in the socket engages an element, such as a male luer fitting 67, on the outflow tubing 18. Alternatively, as shown in FIGS. 14A, 14B, 16, and 17, the socket element 54 may selectively engage an adapter element 34 of the microbore tubing assembly. It is understood that various other embodiments may accomplish the same purpose, which is to engage the distal end of the syringe and/or adapter element 34 of the microbore tubing assembly. For example, an overhanging lip (not shown) disposed on the distal end of the frame 12 may provide antisiphon protection by preventing proximal movement of the barrel under conditions of negative pressure.

One advantage of this embodiment is that the geometry and/or dimensions of the adapter element 34, for example, can be specifically designed to fit a desired driver device. Further, a distal end of frame 12 can include an angled ramp portion 65 which will eject from the driver any syringe that is too large or too small for the driver or any syringe which has mounted to it a tubing assembly with an adapter element 34 which is non-cooperating with socket element 54.

Figure 14A:
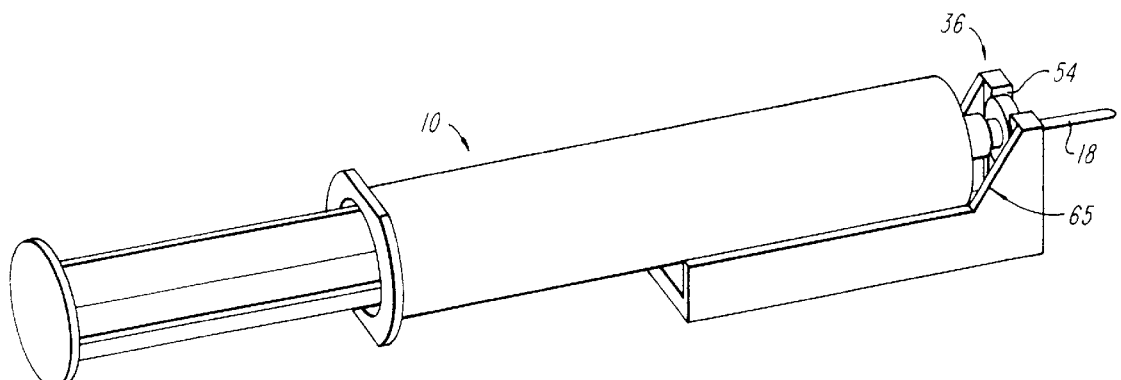
FIG. 14A illustrates a syringe mounted within the front end of the driver device constructed according to one embodiment of the invention.
Figure 14B:
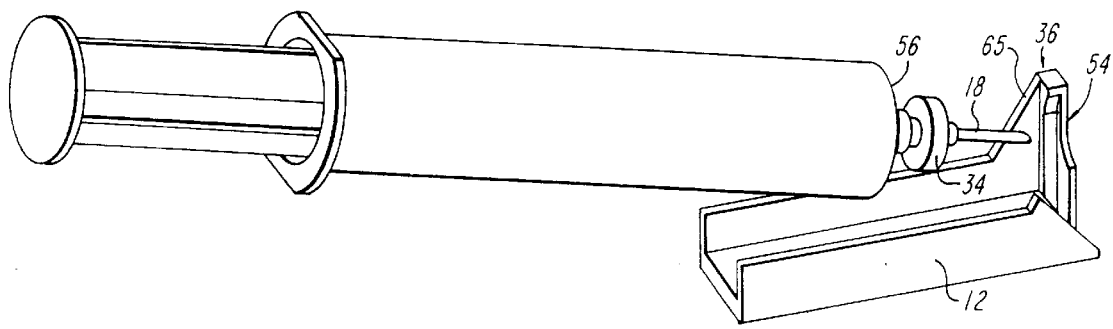
FIG. 14B is a perspective view of a front end, partially cut away, of the driver device illustrated in FIG. 14A.

As illustrated in FIGS. 14A and 14B, a syringe can be mounted within frame 12 by angularly inserting the distal end 56 of the syringe into the syringe mounting element 36. Next, the syringe is forced downwardly until the syringe plunger is properly positioned adjacent the piston (not shown).

Figure 10:
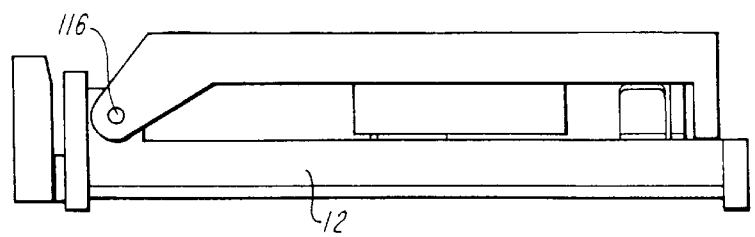
FIG. 10 is a side view of another embodiment of a syringe driver device constructed according to the present invention, having a folding frame shown in the closed position.
Figure 11:
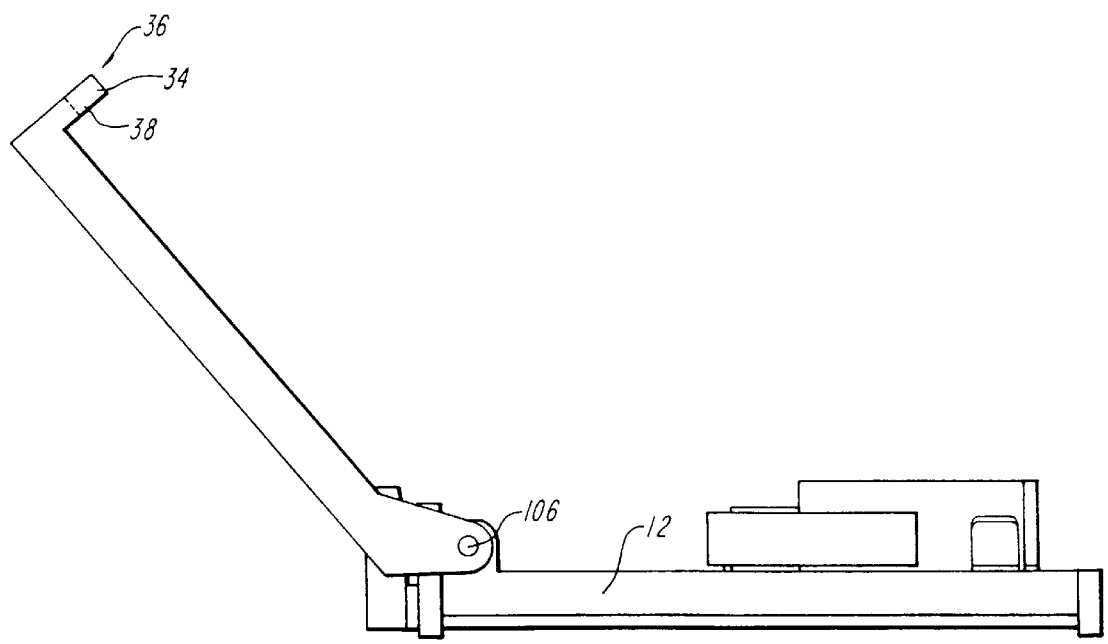
FIG. 11 is a side view of the syringe driver device of FIG. 10, in the partially opened position.

FIGS. 10–12 illustrate an embodiment of the invention in which frame 12 may include a hinge 106 to facilitate folding of the frame. As illustrated in FIGS. 10–12 the syringe securing element 36 is formed by a socket 54 having an aperture 58 which accommodates a distal end 25 of syringe 16 or a proximal end of the tubing assembly.

FIG. 13 illustrates a similar embodiment in which frame 12 is telescoping rather than folding. The frame includes a female portion 12A and a male portion 12B. A detent tab 121 is formed in a forward end of frame portion 12A. In the open position the detent 121 extends through an aperture 123 formed in the frame portion 12A to lock the frame in the open position. The frame can be closed by simply depressing tab element 121 and sliding frame portion 12B within frame portion 12A.

FIGS. 3A through 3D sequentially illustrate the manner in which the driver device of the invention may be utilized, e.g., to deliver the first of a total of four medication doses.

Before the syringe 16 is mounted, the carriage 14 is placed in its fully retracted position at the proximal end 27 of the track 28. Proper insertion of the syringe places the syringe plunger disk 26 so that it is adjacent to the extended carriage piston 68 and contained by the two anti-siphon latches 78. (See FIG. 3A). The extension of the carriage piston 68 is caused by force applied to it by the main spring 66 and is limited by an internal stop (e.g., the collar 90 of the piston). A length of microbore tubing 18 of known dimensions (i.e., length and internal diameter) and performance (i.e., resistance to flow of a specified fluid) is connected to the outlet port 22 of the syringe.

Figure 3A:
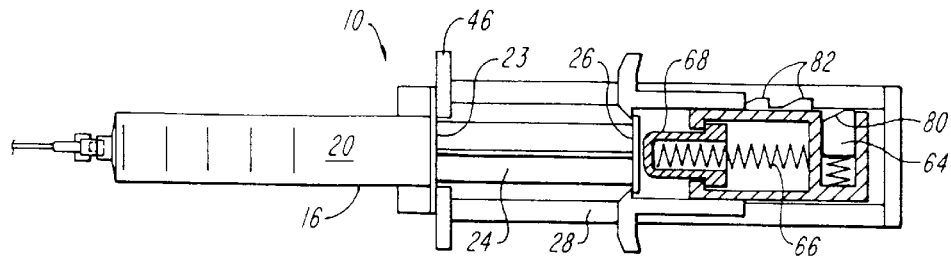
FIGS. 3A through 3D schematically illustrate the operation of the syringe driver assembly shown in FIG. 1.
Figure 3B:
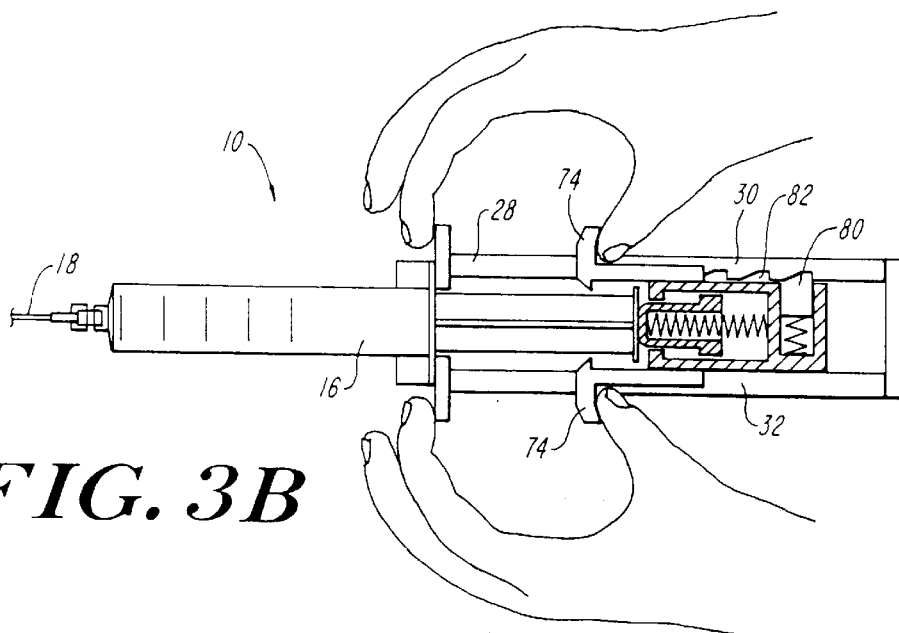
Figure 3C:
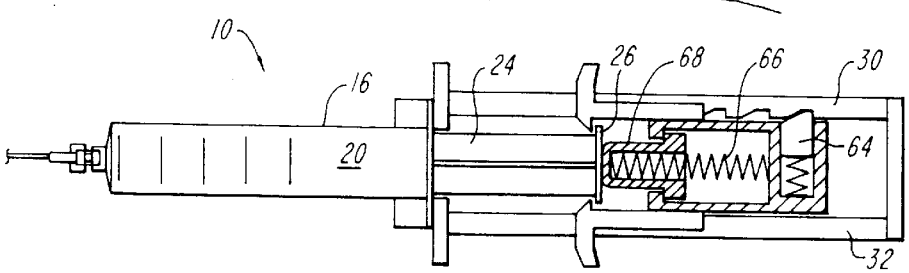
Figure 3D:
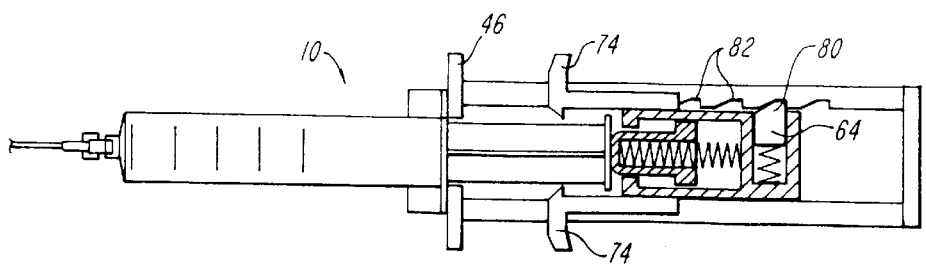

As shown in FIG. 3B, to activate the device, initiating flow of the first dose of fluid, the carriage is advanced forwardly (distally) along the track 28 by manual external force until the pawl 80 engages a desired detent 82 in the track. The carriage piston 68 exerts a force on the syringe plunger 24 and neither the piston nor the plunger can advance due to the presence of fluid in the syringe, the flow of which is restricted by the small diameter of the microbore tubing. This action causes the main spring 66 within the carriage to compress and thereby to apply a driving force to the plunger through the piston. As the carriage piston 68 becomes fully retracted into the carriage, the sliding pawl 80 in the carriage is forced into a detent 82 in the track by an auxiliary pawl biasing spring (not shown), thereby preventing the main spring 66 from forcing the carriage backwards (proximally) when the external force is removed.

As force is now being applied to the disk 26 of syringe plunger 24, fluid will be expelled through the outlet port 22, with a flow rate dependent on the spring force and the resistance of the outflow tubing 18. The syringe plunger 24 and the carriage piston 68 will advance together until the piston is in the fully extended condition in which the collar of the piston contacts the interior distal wall 98 of the carriage. (See FIG. 3C.) Once this condition is achieved, no further force is applied against the syringe plunger and thus fluid flow is stopped. Additional doses are initiated in turn by repeating the action of advancing the carriage to the next detent by manual applied force. (See FIG. 3D.)

The design of the pawl and the detents in the track, shown in FIGS. 8 and 9, and the biasing force of the auxiliary pawl biasing spring (now shown) are optimized for several considerations. First, a rearward force of the main spring will not free the pawl from a detent. Second, only a moderate advancing force is needed to lift the pawl out of a detent, such as by a human user advancing the carriage distally to begin medication delivery. Third, the force needed to lift the pawl out of a detent is sufficient to resist previously described typical negative pressures within the syringe barrel as may act on the locking elements through the plunger disk, anti-siphon stop elements 78 and carriage housing 15. Fourth, the detents are so positioned that, until a given dose is completed, it is impossible to advance the pawl into the detent corresponding to the following dose. If such an attempt is made, the carriage will advance only a limited distance and will spring back to its correct positions as soon as the external force is removed.

If a dose is to be delivered from a partially-filled syringe (e.g., containing, for example, only two of four possible 10-ml doses), the user first observes (using the graduated markings on the syringe barrel) the fill volume of the syringe, in this instance 20 ml. The carriage is then advanced (by depressing release button 64) distally along the rails of the frame, with a manual sliding motion until the pawl engages the detent corresponding to the locked, non force-applying position for a syringe filled to 20 ml. Preferably, a rail (30)-mounted label (not shown) assists the user in so positioning the carriage. The syringe is then inserted, and the spring is actuated for dose delivery, as described above. Confirmation of dose completion is visual by the user, involving observation of device status and plunger tip position with respect to the graduated markings on the syringe barrel.

One feature of the driver device of the invention is that it delivers multiple doses of fluid from a single syringe and that delivery of each dose is initiated by recompressing a drive spring by a simple, individual, manual action such that inadvertent delivery of multiple doses by an individual action is impossible.

Another feature of the driver device of the invention is that one is able to advance the carriage by applying manual force to the two adjacent grip flanges 74 on the carriage and the two adjacent gripping flanges 46 that form part of the syringe mounting element 36. These elements allow the user to grip the device with the thumb and forefinger of both hands and easily to apply sufficient force to advance the carriage. These grips are positioned so that they are within the natural range of motion of an ordinary adult hand. The apparatus does not require additional space or clearance during the operation of advancing the carriage.

An additional feature of the invention relates to removal of the syringe and retraction of the carriage. After all doses have been expelled from the syringe, the syringe may be lifted away from the apparatus with a snapping action. The release button 64 on the side of the carriage, connected to the pawl 80, is depressed causing the pawl 80 to retract into the carriage body. While holding the release button down, the user may easily slide the carriage to its fully retracted position at the proximal end of the frame 12 so that a new syringe may be inserted.

As noted above, and as illustrated in FIGS. 1 through 5, the driver device of the invention includes an anti-siphon element which prevents movement of the plunger independent of movement of the carriage or the force applying element. This element is intended to prevent the syringe plunger from being drawn into the syringe barrel if negative pressure is applied to the syringe outlet port via the connecting tubing, causing an inadvertent delivery of additional fluid. In one embodiment, described above, the anti-siphon element comprises of a pair of latches 78 formed on the internal surfaces of grip flanges 74 that constrain the syringe plunger disk. The gripping flange 46, in cooperation with the distal flange 48 helps to constrain the syringe flange 23. The combination of these elements prevents the plunger 24 from moving forward into the syringe barrel 20 after a dose is completed, and also prevents the syringe barrel 20 from sliding backwards over the plunger.

The shape of the latches 78 is such that if syringe plunger disk 26 is not fully constrained by the latches 78 during insertion into the device, a sharp advancing force, manually applied, will cause the latches 78 to snap over the plunger disk 26 and to be properly engaged by the latches. The first dose cannot be initiated until this action has been taken.

Figure 16:
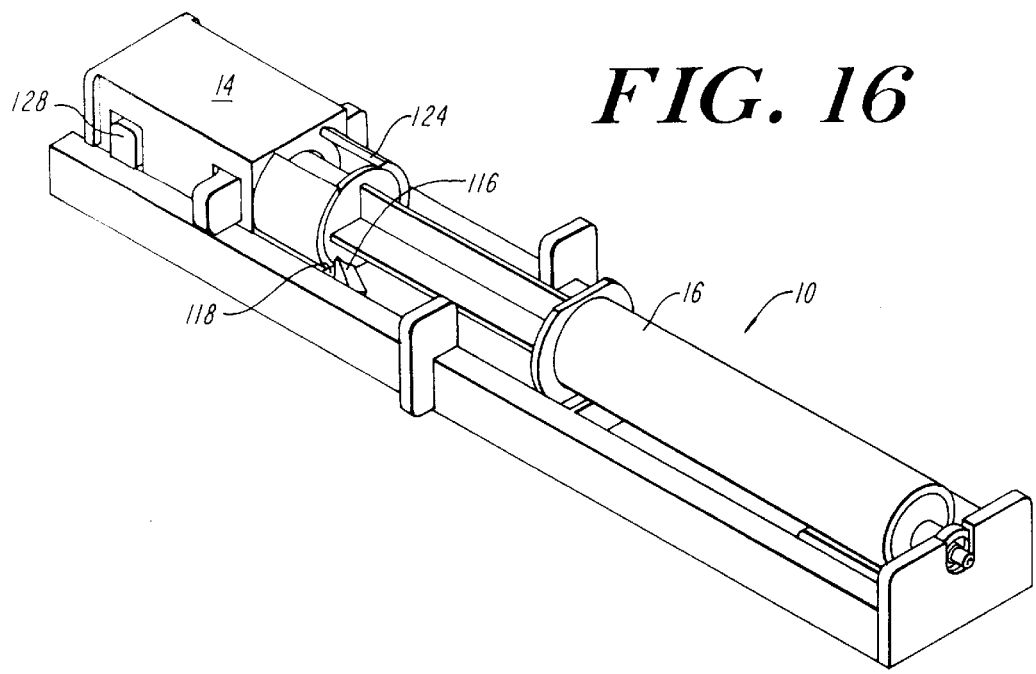
FIG. 16 illustrates another embodiment of the driver device of the invention.
Figure 17:
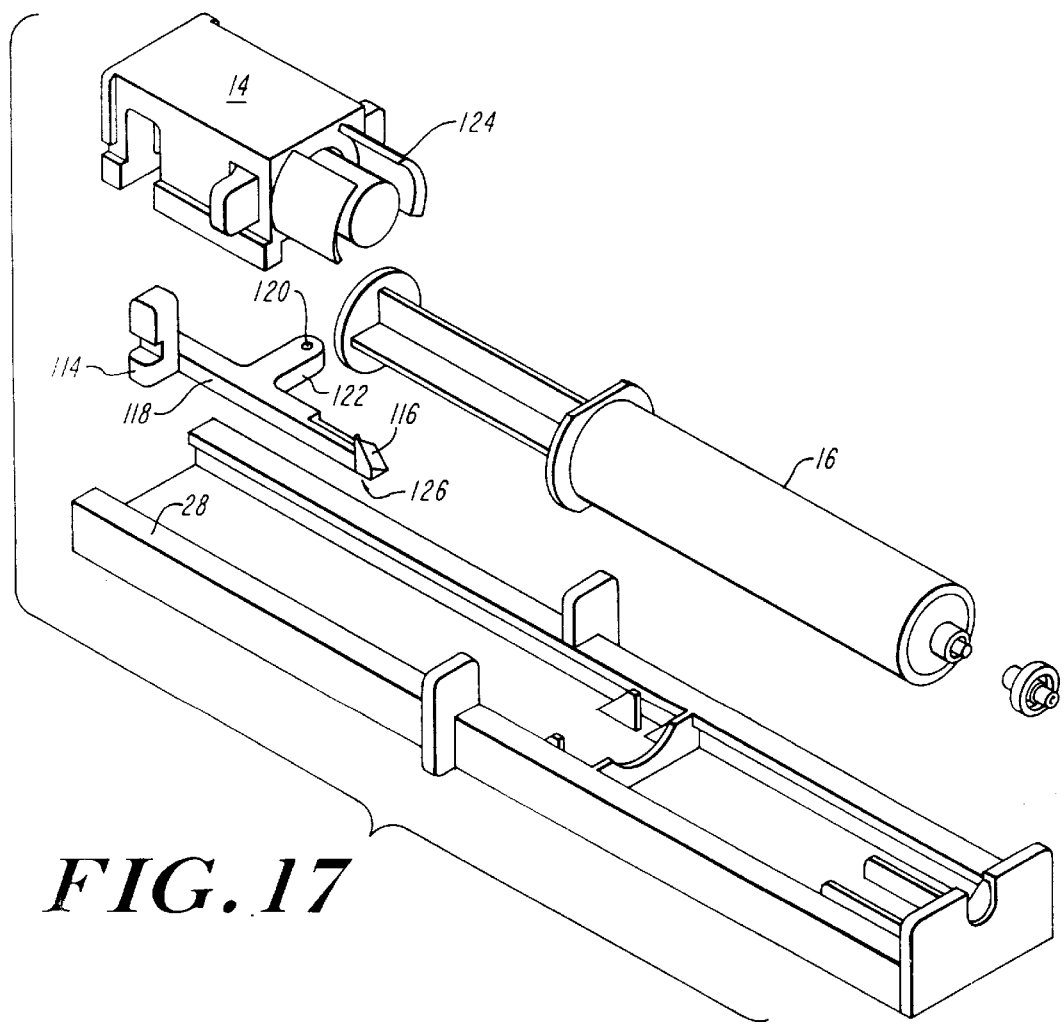
FIG. 17 is an exploded view of the driver device of FIG. 16.

In another embodiment, illustrated in FIGS. 16 and 17, a pivoting arm 118 has a substantially centrally located pivot 120 mounted on a laterally protruding portion 122 of the arm. A proximal end of arm 118 includes a ratcheting pawl 114 while a distal end of arm 126 includes a tapered catch 116. The arm 118 mounts within carriage 14, as shown in FIGS. 18 and 19, such that a spring mechanism (not shown) biases the pawl 114 into contact with detents (not shown) in the track 28. The catch 116 engages the syringe plunger disk 26 whenever the plunger disk 26 is disposed within plunger housing 124 appended to the distal end of carriage 14.

The geometry of the pivoting arm 118 is such that any pulling force on the catch 116 (due to a potential siphoning action) tends to increase the holding force on the detent and thus prevents movement of the carriage. When a user presses the release button 128, which is attached to the pawl, both the pawl 114 and the catch 116 are disengaged, allowing the carriage 14 to be retracted and the syringe to be released for unloading.

One of ordinary skill in the art will appreciate that further embodiments having similar geometries involving both pivoting and sliding devices can produce the same combination of ratcheting and anti-siphoning actions.

An additional feature of the invention is that the spring force applied to the syringe plunger 24 does not change significantly during the travel required to deliver a dose. Accordingly, the flow rate also does not change significantly during delivery of the dose. This is accomplished by three means. First, as described above, the space provided for the main compression spring 66 is relatively long, despite the compact dimensions of the device. This is partly the result of the use of a hollow carriage piston 68, enabling a portion of the spring to reside within the piston. Second, the spring is compressed to less than about half of its unstressed length before being assembled into the carriage. The additional compression of the spring required to advance the carriage during use is only a small fraction of the total compression applied to the spring, resulting in only a small change in reaction force. Further, the spring is recompressed for each dose. Because the spring need only be compressed sufficiently to deliver a single dose, rather than multiple doses, it must be compressed only a small amount for subsequent doses in addition to the compression provided during assembly of the apparatus.

A further advantage of the driver device of the invention is that a simple coil spring is preferably employed as the main spring 66. This spring acts directly in line with the syringe plunger, minimizing frictional forces that might act to disturb the force applied to the syringe.

Because the invention as described depends on the fluid resistance in the connecting tube to control flow rate, it is important that microbore tubing of proper internal diameter be employed. Many operational strategies, such as co-packaging of pre-filled medication containing syringes with appropriate microbore tubing, may be employed to ensure safe practice. In some applications it may be appropriate to mechanically dedicate syringe drivers of a particular design to a specific type, or family of types, of precision microbore tubing. In one such embodiment, shown in FIGS. 14A and 14B, the adapter element 34 of the microbore tubing assembly can have a non-standard geometry and/or dimensions that are adapted to fit only within complementarily sized and shaped sockets 54 of the syringe mounting element 36, as described above.

Figure 15A:
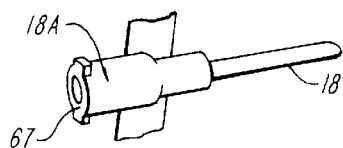
FIG. 15A is a detailed view of a male luer lock fitting.
Figure 15B:
FIGS. 15B and C are detailed views of alternative adapter elements useful with the microbore tubing assembly.
Figure 15C:
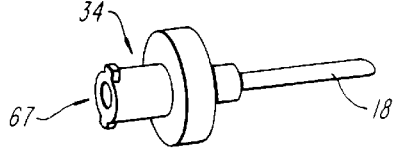

FIG. 15A illustrates a typical male luer fitting 67 which may form a proximal end of the microbore tubing assembly 18 to facilitate connection to the syringe. FIGS. 15B and C illustrate different embodiments of an adapter element 34 for a microbore tubing assembly 18. In these embodiments the adapter is illustrated to be generally oval or circle-shaped, however various other geometries may be used as well. Proximal to adapter 34 is a male Luer lock fitting 67 which can mate with outlet tip 22 and female luer components of syringe distal end 56.

In one embodiment, filled syringes are distributed with a tubing set attached or in a combined package. Operating protocol would require that such syringes always be used with the tubing sets with which they are packaged, and that any unused syringes or tube sets must be disposed of or returned to the distributor.

Table 1 illustrates the approximate spring force and length requirements for use of 20 cc and 60 cc syringes, in which units are in inches and pounds. The smaller syringe requires lower force because of its smaller piston area. By appropriate choice of spring wire diameter and spring length and pitch, a ratio of maximum to minimum force can be maintained comparable to that used with the 60 cc syringe, without greatly extending the working spring length.

Typically, spring force of about 8 pounds is suitable for use with a 60 cc syringe.

TABLE 1

SPRING CALCULATIONS for 10 cc doses from 60 cc and 20 cc syringes

| | (60 cc) | (20 cc) | | (60 cc) | (20 cc) |
|---|---|---|---|---|---|
| d (wire diameter) | 0.048 | 0.033 | plunger diameter | 1.05 | 0.75 |
| D (coil diameter) | 0.5 | 0.5 | plunger area | 0.865901 | 0.441786 |
| n (number of turns) | 20 | 16 | F1 (min force) | 6 | 3.061224 |
| G (shear modulus) (302 Stainless) | $10^7$ | $10^7$ | F2 (max force) | 8 | 4.081633 |
| | | | dx (x1 − x2) | 0.775 | 1.3265 |
| K (spring constant) (from spring geometry) | 2.654208 | 0.741201 | K (spring constant) (from load requirements) | 2.580645 | 0.769249 |
| | | | x1 (deflection at F1) | 2.325 | 3.9795 |
| | | | x2 (deflection at F2) | 3.1 | 5.306 |
| | | | Lfree (min. free length) | 4.156 | 5.8868 |
| | | | Lstart (length at x1) | 1.831 | 1.9073 |
| | | | pitch at Lfree | 0.2078 | 0.367925 |
| | | | pitch at x1 | 0.09155 | 0.119206 |
| | | | pitch at x2 | 0.0528 | 0.0363 |

The flow rate through a circular tube under laminar conditions is determined by Poisseuille's law, which can be stated as:

$$Q = \frac{\pi r^4}{8\mu L}\Delta p$$

where Q is the volumetric flow rate, r is the internal radius of the tube, $\mu$ is the fluid viscosity, L is the length of the tube, and p is the pressure drop along the tube length. The pressure drop can be expanded as:

$$\Delta p = p_i - p_o + \rho g z$$

where $p_i$ is the applied pressure at the inlet end, $p_o$ is the applied pressure at the outlet end, is the fluid mass density, g is the gravitational constant, and z is the difference in height between the two ends of the tube. In the present case, Po is the venous blood pressure of the patient (typically less than 10 cm $H_2O$), and z is the height of the syringe relative to the patient's body.

The inlet pressure, pi, is the force, F, acting on the syringe plunger divided by the plunger surface area, A, and less the friction loss between the plunger and syringe wall, n. The force generated by the compressed spring is known from Hooke's law. In this case Hooke's law may be written as:

$$F = k(l_p + l_d)$$

where k is the spring constant (essentially the stiffness of the spring), $l_p$ is the pre-load deflection applied during assembly, and $L_d$ is the additional deflection applied to activate a dose. Mechanical considerations require that $l_p$ always be somewhat less than the unloaded spring length, particularly for compression springs. The value of $L_d$ is at a maximum at the start of a dose, and goes to zero at the completion of a dose. The design of the present invention, as described previously, provides for $L_d$ to be small compared to $L_p$, and, as can be seen from the above equation, this minimizes the change in force during a dose.

The previous equations can be combined to obtain:

$$Q = \frac{\pi r^4}{8\mu L}\left[\frac{k(l_p + l_d)}{A} - n - p_o + \rho g z\right]$$

For maximum consistency, the values for k, $l_p$, and $L_d$ should be large enough, relative to A, that the other terms within the brackets have a negligible effect on the flow rate. It should be noted that this analysis is only applicable for certain spring types; Hooke's law does not apply to "Neg'ator" type springs, and is only approximate for stretchable rubber springs, which can exhibit highly non-linear behavior.

It is understood that various modifications can be made to the invention described and claimed herein without departing from the intended scope thereof. All references noted herein are expressly incorporated by reference herein in their entirety.

What is claimed is:

1. A syringe driver device, adapted to engage and impart forces to a syringe to dispense fluid from within the syringe, comprising:

a first member having proximal and distal ends;

a selectively positionable second member engageable with the first member adjacent to the proximal end of the first member, the second member having proximal and distal ends;

a syringe, removably mountable within the first member between the distal end of the first member and the distal end of the second member, the syringe including a fluid containing barrel with a flange at a proximal end thereof, an outlet tip at a distal end of the barrel and a moveable plunger, including a disk portion at a proximal end thereof and a tip portion at a distal end thereof, slidably disposed within the barrel for movement between withdrawn and fully inserted positions;

a force applying element, associated with the distal end of the second member, the force applying element being adapted to engage and apply force to the plunger disk; and a spring element disposed substantially internally within the second member and applying a biasing force to the force applying element.

2. The device of claim 1 further comprising a syringe securing mechanism effective to engage and maintain the syringe within the first member.

3. The device of claim 1 further comprising at least one microbore tubing assembly having proximal and distal ends with a fluid passageway extending therebetween, the proximal end including an adapter mechanism to facilitate detachable coupling to the end of the syringe.

4. The device of claim 2 wherein the syringe securing mechanism includes a distal securing element and a proximal securing element.

5. The device of claim 4 wherein the distal securing element of the syringe securing mechanism comprises a yoke, including a slot formed therein transverse to a longitudinal axis of the first member, the slot having a size and geometry sufficient to secure and seat a syringe flange.

6. The device of claim 4 wherein the distal securing element of the syringe securing mechanism comprises a socket element at a distal end of the first member, the socket element having an internal geometry of a size and shape to cooperatively engage the distal end of the syringe.

7. The device of claim 4 wherein the distal securing element of the syringe securing mechanism comprises a socket element at a distal end of the first member, the socket element having an internal geometry of a size and shape to cooperatively engage the adapter mechanism of the microbore tubing assembly.

8. The device of claim 1 wherein the force applying element is retractable within the second member.

9. The device of claim 1 wherein the spring element is a compression spring oriented substantially parallel with a longitudinal axis of the first member.

10. The device of claim 4 wherein the adapter mechanism of the microbore tubing assembly includes a Luer lock connection, and further includes an external geometry.

11. The device of claim 10 wherein the microbore tubing assembly includes a plurality of microbore tubing assemblies, each having a fluid passageway with different inner diameters.

12. The device of claim 11 wherein the external geometry of the adapter mechanism varies with the inner diameter of the fluid passageway of the microbore tubing.

13. The device of claim 11 wherein the dimensions of the external geometry of the adapter mechanism vary with the inner diameter of the fluid passageways of the microbore tubing.

14. A syringe driver device, adapted to engage and impart forces to a syringe to dispense fluid from within the syringe, comprising:

a first member having proximal and distal ends;

a selectively positionable second member, the second member being engageable with the first member and having proximal and distal ends with an aperture formed in the distal end thereof;

a force applying element, disposed within the second member, the force applying element being distally biased; and a spring element disposed internally within the second member and applying a biasing force to the force applying element.

15. The device of claim 14, further comprising a syringe securing means for engaging and maintaining a syringe within the first member.

16. A syringe driver system, adapted to engage and impart forces to a syringe to dispense fluid from within the syringe, comprising:

a first member having proximal and distal ends;

a second member, having proximal and distal ends and being engageable with the first member;

a syringe removably mountable within the first member between the distal end of the first member and the distal end of the second member, the syringe including a fluid containing barrel with a flange at a proximal end thereof, an outlet tip at a distal end of the barrel and a plunger slidably disposed within the barrel for movement between withdrawn and fully inserted positions;

a force applying element associated with the distal end of the second member, the force applying element being distally biased within the second member and being adapted to selectively apply force to the plunger disk;

a spring element disposed substantially internally within the second member and applying a biasing force to the force applying element;

a syringe engaging mechanism effective to engage and maintain the syringe within the first member; and at least one microbore tubing assembly, the at least one microbore tubing assembly having a proximal and a distal end with a fluid passageway extending therebetween, the proximal end including an adapter mechanism to facilitate detachable coupling to the end of the syringe.

17. The system of claim 16, wherein each of the at least one microbore tubing assemblies has a different fluid passageway inner diameter and an adapter mechanism external geometry and size specific to the inner diameter of the microbore tubing.

* * * * *

UNITED STATES PATENT AND TRADEMARK OFFICE
CERTIFICATE OF CORRECTION

PATENT NO. : 5,954,695
DATED : September 21, 1999
INVENTOR(S) : Nathaniel M. Sims et al.

It is certified that error appears in the above-identified patent and that said Letters Patent is hereby corrected as shown below:

Col. 1, line 8: Reads: "Ser. No. 60/002771"

Should read: --Ser. No. 60/002,771--

Col. 12, line 35: Reads: "of the tube $\mu$is,"

Should read: --of the tube $\mu$ is--

UNITED STATES PATENT AND TRADEMARK OFFICE
CERTIFICATE OF CORRECTION

PATENT NO. : 5,954,695
DATED : September 21, 1999
INVENTOR(S) : Nathaniel M. Sims et al.

It is certified that error appears in the above-identified patent and that said Letters Patent is hereby corrected as shown below:

Col. 12, line 59:  Reads: " and $L_d$"

Should read: -- and $l_d$ --

Col. 12, line 62:  Reads: "The value of $L_d$"

Should read: --The value of $l_d$ --

Col. 12, line 65:  Reads: "provides for $L_d$ to be small compared to $L_p$"

Should read: --provides for $L_d$ to be small compared to $l_p$--

Signed and Sealed this

Twenty-second Day of May, 2001

Attest:

NICHOLAS P. GODICI

Attesting Officer    Acting Director of the United States Patent and Trademark Office